United States Patent [19]
Matsukawa et al.

[11] Patent Number: 5,948,665
[45] Date of Patent: Sep. 7, 1999

[54] HEXOKINASE OBTAINED FROM THERMOPHILIC YEAST *KLUYVEROMYCES FRAGILIS*

[75] Inventors: Hirokazu Matsukawa; Tuyosi Fujita, both of Osaka, Japan

[73] Assignee: Oriental Yeast Co. Ltd., Tokyo, Japan

[21] Appl. No.: 08/799,659

[22] Filed: Feb. 11, 1997

[30] Foreign Application Priority Data

Feb. 16, 1996 [JP] Japan ................................ 8-052532

[51] Int. Cl.$^6$ .............................. C12N 9/12; C12N 1/14; A61K 38/47
[52] U.S. Cl. .................... 435/194; 435/255.1; 424/94.61
[58] Field of Search ................................. 435/194, 193, 435/255.1, 15; 424/94.61, 94.6

[56] References Cited

FOREIGN PATENT DOCUMENTS

| | | |
|---|---|---|
| 0 253 520 | 1/1988 | European Pat. Off. . |
| 0 666 323 | 8/1995 | European Pat. Off. . |
| 55-099190 | 7/1980 | Japan . |
| 9400836 | 1/1996 | Netherlands . |

OTHER PUBLICATIONS

Garcia et al. "Caracterizacion de levaduras por enzimoforesis", Interferon y Biotechnologia (1985) 2(2): 129–136, 1985.

Hutchinson et al. "Hexokinase of the adult dog heartworm, Dirofilaria Immitis" Comp. Biochem. Physiol. (1977) 58B: 131–134, 1977.

I. Balesteros et al., "Optimization of the Simultaneous Saccharification and Fermentation Process Using Thermotolerant Yeasts.", Applied Biochemistry and Biotechnology, vol. 39/40, pp. 201–211 (1993).

Abstract of Japanese application No. 55–099190, published Jul. 28, 1980 from Derwent, accession No. 80–633830.

Abstract of Japanese application No. 05–111396, published May 7, 1993 from Derwent, accession No. 93–184816.

Clinical Chemistry, vol. 20 No. 4, pp. 247–254, 1991.

Clinical Chemistry, vol. 19 No. 2, pp. 185–208, 1990.

*Primary Examiner*—Jon P. Weber
*Assistant Examiner*—Susan Hanley
*Attorney, Agent, or Firm*—Browdy and Neimark

[57] ABSTRACT

The present invention relates to a hexokinase that is stable in solution whether in the presence or the absence of glucose. The present enzyme is obtained from a culture of the thermophilic yeast, Kluyveromyces. It can be used for determination of ATP and glucose, and for determination of a biological component which produces ATP or glucose (e.g. creatine kinase).

6 Claims, 4 Drawing Sheets

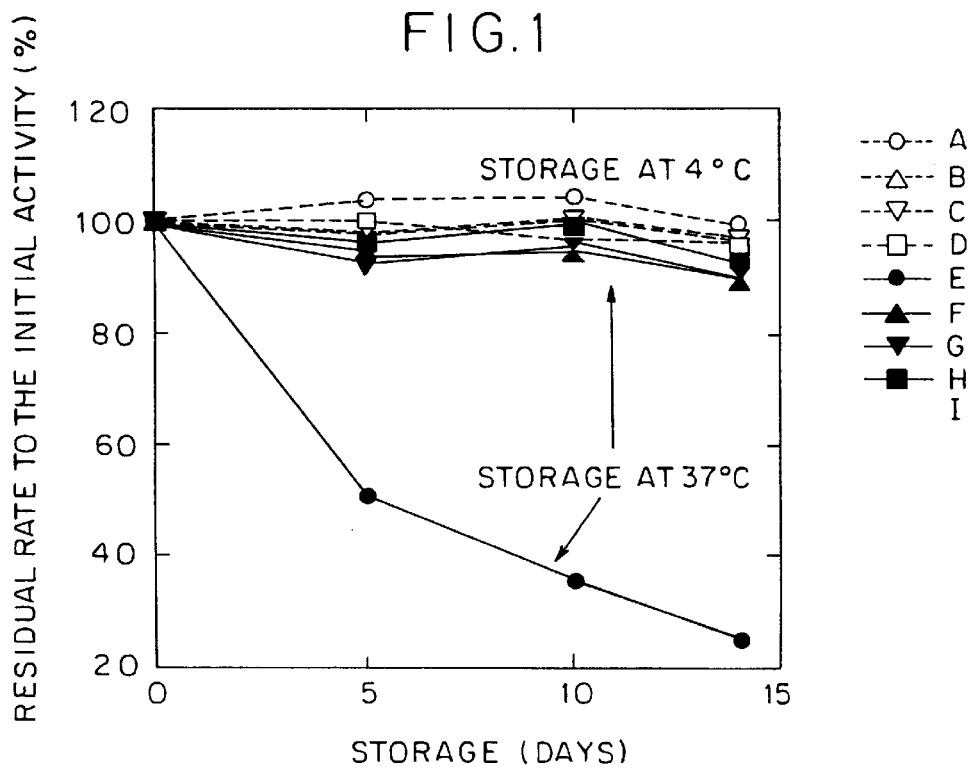
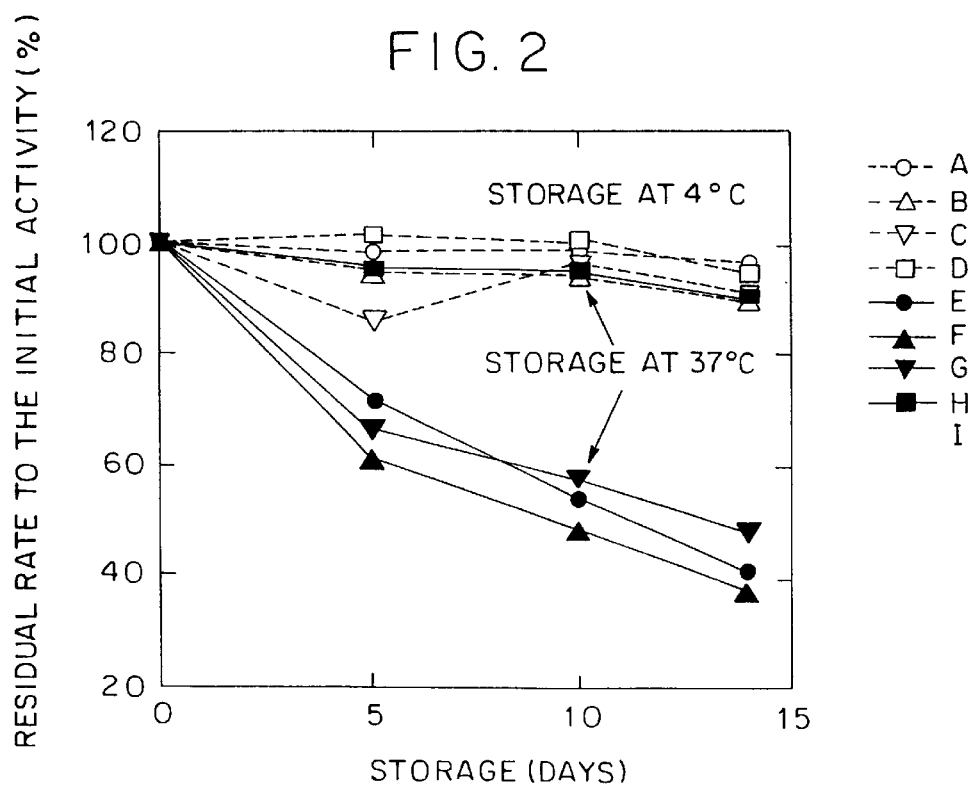

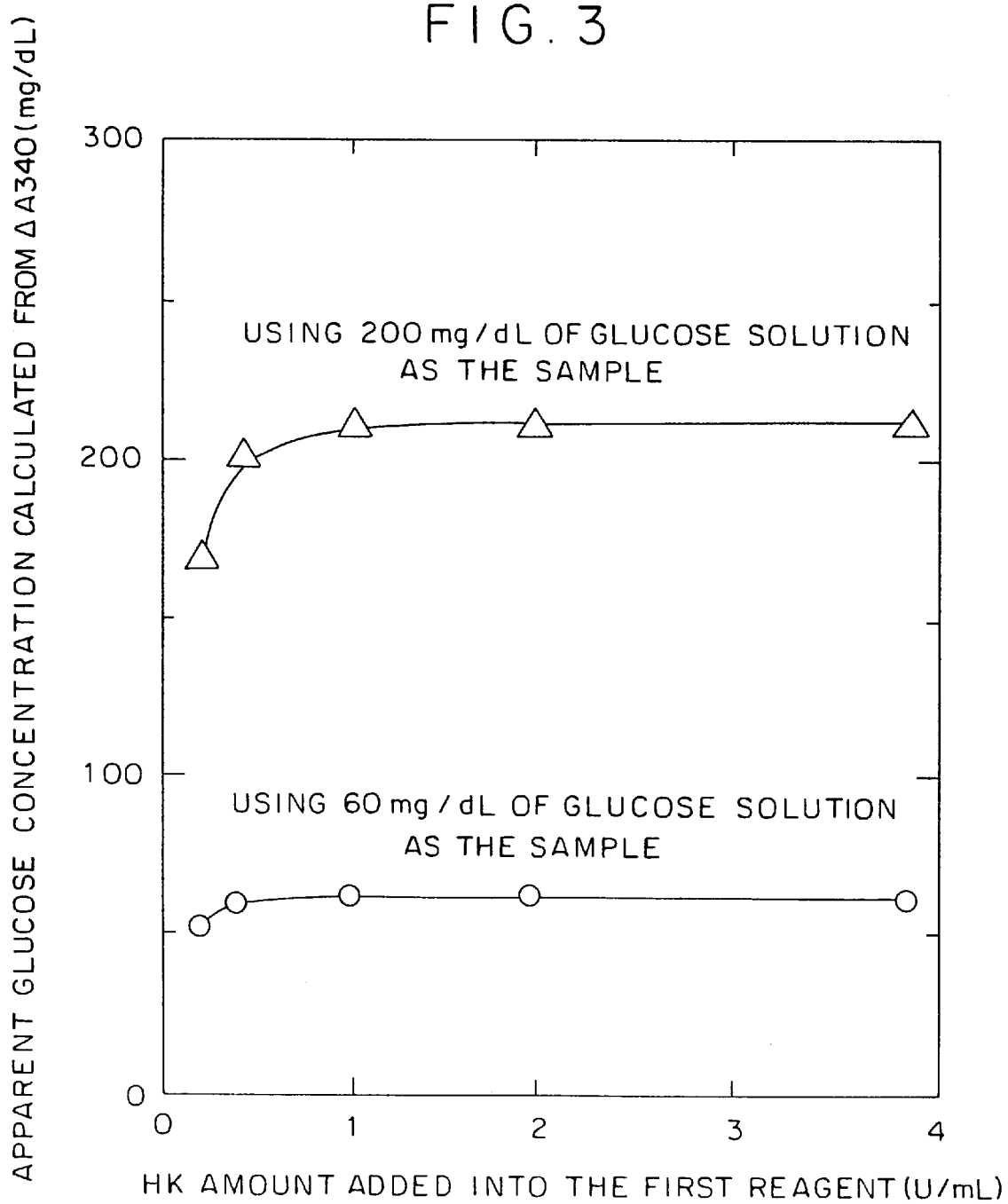

HEXOKINASE OBTAINED FROM THERMOPHILIC YEAST KLUYVEROMYCES FRAGILIS

FIELD OF THE INVENTION

The present invention relates to a novel hexokinase of excellent stability in solution, its preparation and its use.

PRIOR ART

Hexokinase (EC 2.7.1.1; hereinafter sometimes referred to as HK) is an enzyme catalyzing the phosphoesterification reaction of hexose such as glucose into hexose-6-phosphate ("Microbiological Dictionary", p978, Aug. 23, 1989, published by Gihodo).

However, the well-known hexokinase at present obtained from any origin is extremely unstable in solution; for instance, when it is stored at 37° C., the residual rate falls to approximately 50% within only 5 days in a buffer of a glucose determination reagent.

Since hexokinase of the prior art is extremely unstable in solution, it cannot be stored for a long term, therefore it must be prepared immediately prior to its use.

That is, the hexokinase in solution cannot be stored at room temperature, and therefore a determination reagent or a kit for determination using it cannot be easily provided.

BRIEF SUMMARY OF THE INVENTION

The present invention was made in order to meet the present requirements to the conventional technique described above, that is, in order to provide HK which can be used previously dissolved in a buffer etc. by the development of a novel HK which can be stored at from room temperature to high temperatures without lowering its activity for a long term even in solution to perform determination easily and rapidly, and in order to reduce the cost by prolonging shelf life.

As a result of intensive study, we have been successful in collecting hexokinase of excellent stability in solution from the cells of a thermophilic yeast belonging to Kluyveromyces, and it has been confirmed that the obtained hexokinase was a novel enzyme which has been previously unknown to achieve the present invention.

The present invention will be described in detail below.

The HK according to the present invention has physico-chemical properties described below, especially superior stability and reactivity as hereunder set forth, and therefore it is an improved HK.

1) The HK of the present invention exhibits excellent stability in storage tests in solution at 37° C. whether in the presence or the absence of glucose.

2) The present HK has high reactivity to glucose, therefore the amount of glucose can be rapidly determined even at low concentrations by a small enzyme amount of said HK.

In order to prepare the HK according to the present invention, it is needed first to ferment and select thermophilic yeast which is able to grow at 35° C. or above, preferably 40° C. or above. As preferable thermophilic yeast, Kluyveromyces, *Candida bovina* IFO 0873 (*Torulopsis bovinna* (ATCC22987)), *C. pintolopesii* IFO 0729 (*T. pintolopesii*), *C. pintolopesii* var *sloofii* IFO 0874, *Arxiozyma telluris* (*Saccharomyces telluris*) IFO 1331, *Pichia augusta* (*Hansenula polymorpha*) IFO 1476, etc. are noted, and an especially preferable thermophilic yeast strain among said yeast is fermented and selected.

For instance, *Kluyveromyces marxianus* IFO 10005, *Kluyveromyces fragilis* IFO 1735 and 1777, etc. can be used advantageously, but the other Kluyveromyces can also be widely used.

Following the description in Applied Biochemistry and Biotechnology Vol.39/40, pp201–211 by I. Ballesteros et al. (1993) etc., these type culture strains are cultured at high temperatures about 45° C. to obtain colonies, the desired strain is selected from the colonies and cultured, and the hexokinase is extracted from the resultant cell paste in the conventional method.

For instance, the cells are collected, crushed, suspended in phosphate buffer, and centrifuged to obtain the supernatant. After its extraction, the HK is purified by a well-known method of purification processes such as chromatography, treatment with ammonium sulfate, and ion exchange treatment, etc.

BRIEF DESCRIPTION OF THE DRAWINGS

FIG. 1 shows residual rates of the HK of this invention in a buffer of a CPK activity determining reagent. CPK is creatine phosphokinase which is identical with CK, creatine kinase.

FIG. 2 shows residual rates of the HK in a buffer of a glucose determining reagent.

FIG. 3 shows enzyme following performance of the HK in determination of glucose.

DETAILED DESCRIPTION OF THE INVENTION

PREPARATION EXAMPLE

Preparation of Hexokinase

Figure 4:
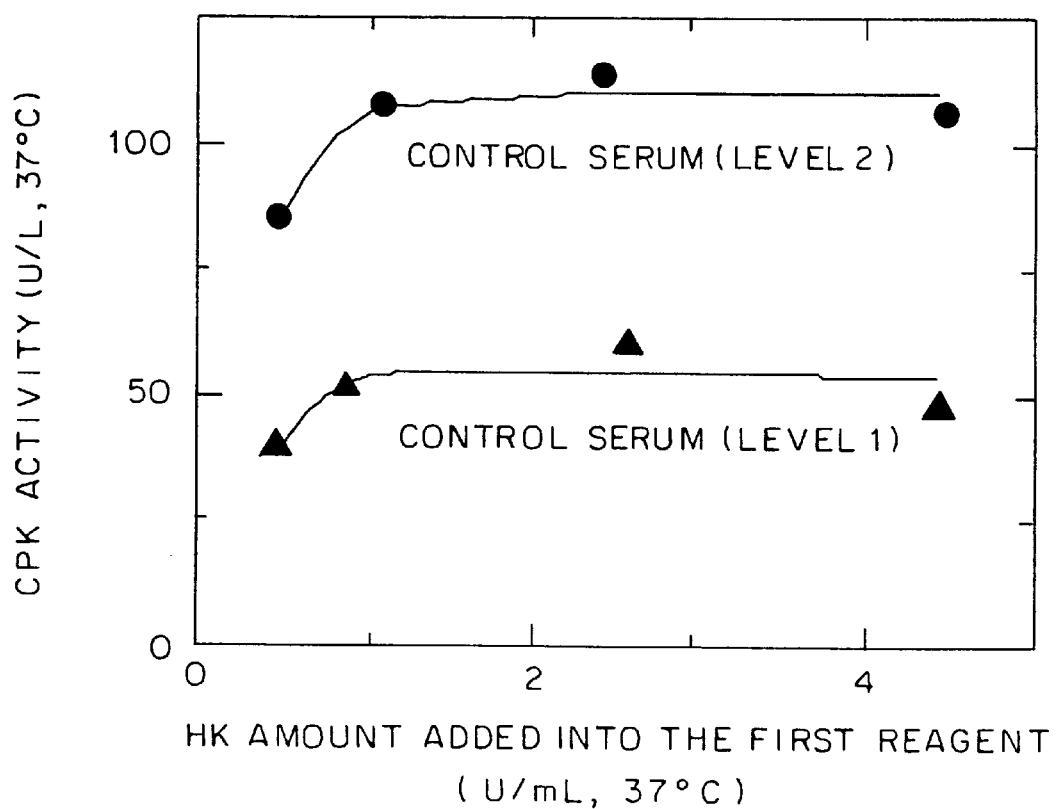
FIG. 4 shows enzyme following performance of the HK in determination of creatine kinase (CPK) activity.

A strain of *Kluyveromyces fragilis* IFO 1777 was cultured, and from the obtained cells of the thermophilic yeast, the novel hexokinase was extracted and purified as follows.

(1) Culture of Thermophilic Yeast, Kluyveromyces Strain

A culture medium comprising the yeast extract (0.3%), malt extract (0.3%), peptone (0.5%), glucose (1%), and agar (1.5%) was adjusted to pH 6.0 and autoclaved, and a suspension of the cells of the type culture of Kluyveromyces was smeared on the agar medium. Then, the medium was allowed to stand at 45° C. overnight to perform colony formation. And then single colonies on the agar medium were picked up with a loop, suspended in the liquid medium described above without containing agar (10 mL) in a test tube, and cultured with shaking at 45° C. overnight. The results of determination of hexokinase (HK) content of the thermophilic yeast strains belonging to Kluyveromyces are summarized in Table 1 below.

TABLE 1

| Strain activity | Result of culture | | Amount of HK |
| | pH of medium | $OD_{600}$ | (at 37° C.) |
| --- | --- | --- | --- |
| IFO10005 | 5.28 | 1.27 | 0.34U |
| IFO 1777 | 4.62 | 5.35 | 5.80 |
| IFO 1735 | 4.67 | 0.97 | 0.25 |

Preparation of a extract solution from the cells was performed in the following manner.

That is, the cells obtained by culturing with shaking in the test tube having 10 mL of the medium was collected by centrifugation, suspended in 5 mL of 20 mM K—PO$_4$ buffer (containing 1 mM 2ME, 0.5 mM EDTA, 0.02% NaN$_3$, and 0.1 mM PMSP; pH 7.5), and treated with an ultrasonic crusher (UD-200; trade name, Tomy Co.) in an ice-water bath for 5 minutes. The resultant suspension bath obtained above was centrifugalized, and the supernatant collected as the HK extract solution.

Determination of the HK enzymatic activity was performed in the following conditions.

Temperature: 37° C.; Instrument: Hitachi U-2,000 spectrophotometer; Wavelength: 340 nm; Composition of the substrate reagent: 0.1 M TEA-HCl (pH 7.5) containing 50 mg/mL of glucose, 5 mM MgCl$_2$, 1 mM ATP, 1 mM NAD+, and 2 U/mL of glucose-6-phosphate dehydrogenase (Leuconostoc).

As concerns the enzymatic activity, 1 unit means the quantity producing 1 μmole of NADH per minute under the reaction conditions given above.

In separation and purification of hexokinase from the cells of the thermophilic yeast, *Kluyveromyces fragilis* (IFO1777) was selected which had the highest yield of the enzyme from among Kluyveromyces strains. Needless to say, strains belonging to Kluyveromyces are not restricted to this culture strain.

*Kluyveromyces fragilis* (IFO1777) was deposited under Budapest Treaty in National Institute of Bioscience and Human-Technology, Agency of Industrial Science and Technology, Ministry of International Trade and Industry of 1–3, Higashi 1 chome, Tsukuba-shi, Ibaraki-ken, 305, Japan on Feb. 6, 1997 and assigned deposit No. FERM BP-5812.

(2) Purification of Hexokinase

In obtaining HK from the cells of a thermophilic yeast, Kluyveromyces, IFO 1777 strain having a high enzyme activity was selected based on the results of the test tube culture mentioned above, and culturing with 3.5 L medium in flasks with shaking was performed by seeding the cell suspension after the test tube culture. By culturing at 45° C. for 9 hours, 30 g wet cells of the thermophilic yeast were collected from the culture suspension by centrifugation. The obtained cells were suspended in 5fold volume of the extract buffer described above, and the HK content of the cultured cells was determined by ultrasonic crushing to give 59 U/g wet cells.

Separation and purification of the HK were performed using the cell-free extract prepared by the ultrasonic crushing treatment as a crude enzyme solution, by ion-exchange chromatography using DEAE-Sephalose CL6B gel, the chromatography again, and gel filtration chromatography of HPLC with TSK gel G3,000 SW column. The sample finally obtained had the specific activity of 169 U/mg protein (calculated on E$_{280}$nm (concentration 1%)=10.0), and the yield based on 100% of the total activity of the cell-free extract solution which was used as the starting material in the enzyme purification was 18.2%.

(3) Property of Hexokinase

As the result of the investigation of enzymatic properties of the HK derived from the cells of Kluyveromyces (IFO1777) based on the HK sample obtained here, the HK had the properties given below and was identified as a novel enzyme that has been unknown so far.

The obtained hexokinase exhibits the physicochemical properties below.

(A) Stability: The hexokinase is stably stored in solution at 37° C. whether in the presence or the absence of glucose. The stability of it provides at least 80% of the residual activity after 7 days at 37° C.

(B) Reactivity: The hexokinase has high reactivity to glucose, therefore the amount of glucose can be rapidly determined even at low concentrations by a small enzyme amount of the HK.

(C) Substrate specificity: The hexokinase has high reactivity especially to glucose and fructose.

The degrees of reactivity based on 100% to glucose were as follows (the substrate concentration of various monosaccharides was 0.1 M in the determination of the substrate specificity).

| | |
|---|---|
| glucose | 100% |
| fructose | 189.4% |
| mannose | 68.1% |
| galactose | 62.2% |
| xylose | 24.3% |
| sorbitol | 6.8% |
| mannitol | 0.1% |

(D) Molecular weight: 60,000 (gel filtration chromatography)

(E) Isoelectric point: PI=4.70 (chromatofocusing)

The hexokinase according to the present invention includes all the enzymes below: an enzyme preparation prepared by purification of the strain culture mentioned above, a recombinant enzyme prepared by introducing a hexokinase gene derived from thermophilic yeast Kluyveromyces, into a host such as *E.coli*, and a modified enzyme prepared by protein cross-linking reaction etc.

The novel hexokinase of excellent stability in solution according to the present invention has the excellent properties described above, and therefore the hexokinase (HK) can be used to advantage in place of HK that has been well-known so far in a variety of conventional methods of determining glucose and/or ATP using a hexonase such as a determination method of glucose using hexokinase combined with glucose-6-phosphate dehydrogenase (G6PD) (HK-G6PD method) etc., and the present invention can advantageously provide an excellent novel determination reagent and a determination kit using it.

As described above, the novel HK according to the present invention can be used to advantage for determination of ATP and/or glucose accurately, rapidly, and inexpensively without skill, and therefore it can be used naturally for a system of direct determination of ATP and/or glucose, and also used to advantage for a system of determination of biological components which produce ATP or glucose, and the present invention can advantageously provide a method of determining said biological components, a determination reagent, and a determination kit characterized by using the HK.

An example of a process for the determination of biological components which produce ATP or glucose is that of creatine kinase (CPK) activity described below:

"A process for the determination of creatine kinase activity comprising bringing a sample into contact with a reaction system containing at least creatine phosphate, ADP, hexokinase or glucokinase, glucose, glucose-6-phosphate dehydrogenase, and coenzyme or coenzyme analogs (e.g., thionicotinamide adenine dinucleotide (hereinafter referred to as thio-NAD) or thionicotinamide adenine dinucleotide phosphate (hereinafter referred to as thio-NADP)), and detecting a detectable change."

As said biological components, in addition to creatine kinase described above, all biological components which produce ATP or glucose in a reaction system can be applied to the present invention.

Hereinafter, description is made of examples according to the present invention.

EXAMPLE 1

Storage Stability of Hexokinase in Solution

The storage stability of hexokinase derived from thermophilic yeast, Kluyveromyces, in a variety of test reagents was determined under the conditions given below. In addition, a variety of hexokinase which were used as the controls and their origin will be described.

HK Enzyme Reagent:
 1) Hexokinase derived from Kluyveromyces (this invention)
 2) Hexokinase derived from *Saccharomyces cerevisiae*, PI (Oriental Yeast Co., Ltd.)
 3) Hexokinase derived from *Saccharomyces cerevisiae*, PII (Boehringer)
 4) Hexokinase derived from Bacillus (Asahi Chemical Industry Co., Ltd.)

Conditions:
 (1) Temperature in storage: 4° C. and 37° C.
 (2) Days in storage: sampling after 0, 5, 10, and 14 days
 (3) Initial amount of HK: 0.5 U/ml (determination at 37° C.)
 (4) Buffers for storage stability tests:
  (a) Buffer for CPK activity determination reagent
   100 mM imidazole acetic acid buffer (pH 6.7) containing 2 mM EDTA, 10 mM magnesium acetate, and 25 mM N-actylcysteine
  (b) Buffer for glucose determination reagent
   100 mM tris hydrochloric acid buffer (pH 7.5) containing 5 mM magnesium acetate In addition, 0.02% sodium azide was added as an antiseptic to the solution for storage tests at 4° C. and 37° C. given above for investigation of storage stability in solution.

(5) Calculation of the degree of storage stability in solution:

The proportion of the residual activity to the initial HK activity was plotted against the storage days to estimate half-life of the varieties of HK based on the rate of residual activity.

The results are shown in FIG. 1 (buffer (a)) and FIG. 2 (buffer (b)), respectively.

EXAMPLE 2

Enzyme Following Performance in Glucose Determination (Which Means Enzymatic Function of Glucose Determination)

In order to confirm the enzyme following performance of hexokinase derived from thermophilic yeast (Kluyveromyces) in glucose determination, a reagent for glucose determination was prepared on the basis of the method of determining glucose and the composition of the reaction reagent in glucose determination described in Clinical Chemistry Vol.20 No.4, p247–254 (1991).

Conditions:
 (1) Sample and blank
 The samples were a standard glucose solution of 200 mg/dL (Denka Seiken Co.) and its solution diluted to 60 mg/dL with 0.9% aqueous solution of NaCl. As the blank 0.9% aqueous solution of NaCl was used.
 (2) Conditions in determination
 Instrument: Cobasfara (trade name, Baxter Co.); Temperature: 37° C.; Wavelength: 340 nm
 (3) Ratio of the sample and the reagents
 Sample: First reagent: Second reagent=4:400:100

(4) Composition of the reagents

|  | First reagent | Second reagent | Concentration of reaction solution |
|---|---|---|---|
| ATP | — | 6 mM | 1.2 mM |
| NADP+ | 1.5 mM | — | 1.2 mM |
| G6PD | 2.5 U/ML | — | 2 U/mL |

Both the First reagent and Second reagent described above were dissolved with 100 mM Tris-HCl buffer (pH 7.5) and containing 5 mM magnesium acetate, respectively.

(5) Determination of HK following performance(*11) in glucose determination
 HK following performance was determined as the relationship between the apparent glucose value after addition of HK of a variety of concentration into the First reagent described above and the HK amount added into the First reagent.

(6) Calculation of apparent glucose value based on $\Delta A_{340}$ variation
 $A_{340}$ was obtained by subtracting the initial absorption at mixing the First reagent and the sample from $A_{340}$ at 3 minutes after starting the reaction by addition of the Second reagent, and the apparent glucose concentration of the sample was calculated.

The results are shown in FIG. 3.

EXAMPLE 3

Enzyme Following Performance in Determination of Creatine Kinase Activity (Which Means Enzymatic Function of Creatine Kinase Activity Determination)

The enzyme following performance of hexokinase derived from thermophilic yeast (Kluyveromyces) in determination of creatine kinase activity was confirmed as follows.

That is, to the composition of the reagent prepared for determination of CK (creatine kinase) activity, the composition of the final reaction solution described in Clinical Chemistry Vol.19 No.2, p185–208 (1990) was applied. The conditions were as follows.

Conditions:
 (1) Sample and blank
 Control serum on the market (Consera and Consera A, Nissui Seiyaku Co.) was used. As the blank, 0.9% aqueous solution of NaCl was used.
 (2) Conditions in determination
 Instrument: Cobasfara; Temperature: 37° C.
 (3) Ratio of the sample and the reagents
 Sample: Purified water: First reagent: Second reagent= 6:4:240:60 ($\mu$L)
 (4) Calculation of CK activity
 $\Delta A_{340}$/min was obtained by the rate assay for 1.5 minute ranging from 2.5 to 4 minutes after mixing the sample and the determination reagents.
 (5) Relationship between CK activity and HK following performance
 The apparent value of CK activity obtained from the time course from the beginning of the reaction by addition of HK of a variety of concentration into the First reagent was plotted against the amount of HK added into the First reagent.

The composition of the reagents used above will be shown in Table 2 given below.

The buffer dissolving the CK activity determination reagents was 100 mM imidazole acetic acid buffer (pH 6.7), containing 2 mM EDTA, 10 mM magnesium acetate, and 20 mM glucose.

TABLE 2

|  | 1st reagent | 2nd reagent | Final concentration |
|---|---|---|---|
| ADP | 2.5 mM | — | 2 mM |
| NAC | 25 mM | — | 20 mM |
| AMP | 6.25 mM | — | 5 mM |
| AP$_5$A | 12.5 μM | — | 10 μM |
| NADP+ | 2.5 mM | — | 2 mM |
| G6PD | — | 15 U/mL | 3 U/mL |
| CP | — | 150 mM | 30 mM |

NAC: N-acetylcysteine, CP: creatine phosphate, CK: creatine kinase

The results are shown in FIG. 4.

Figure 5:
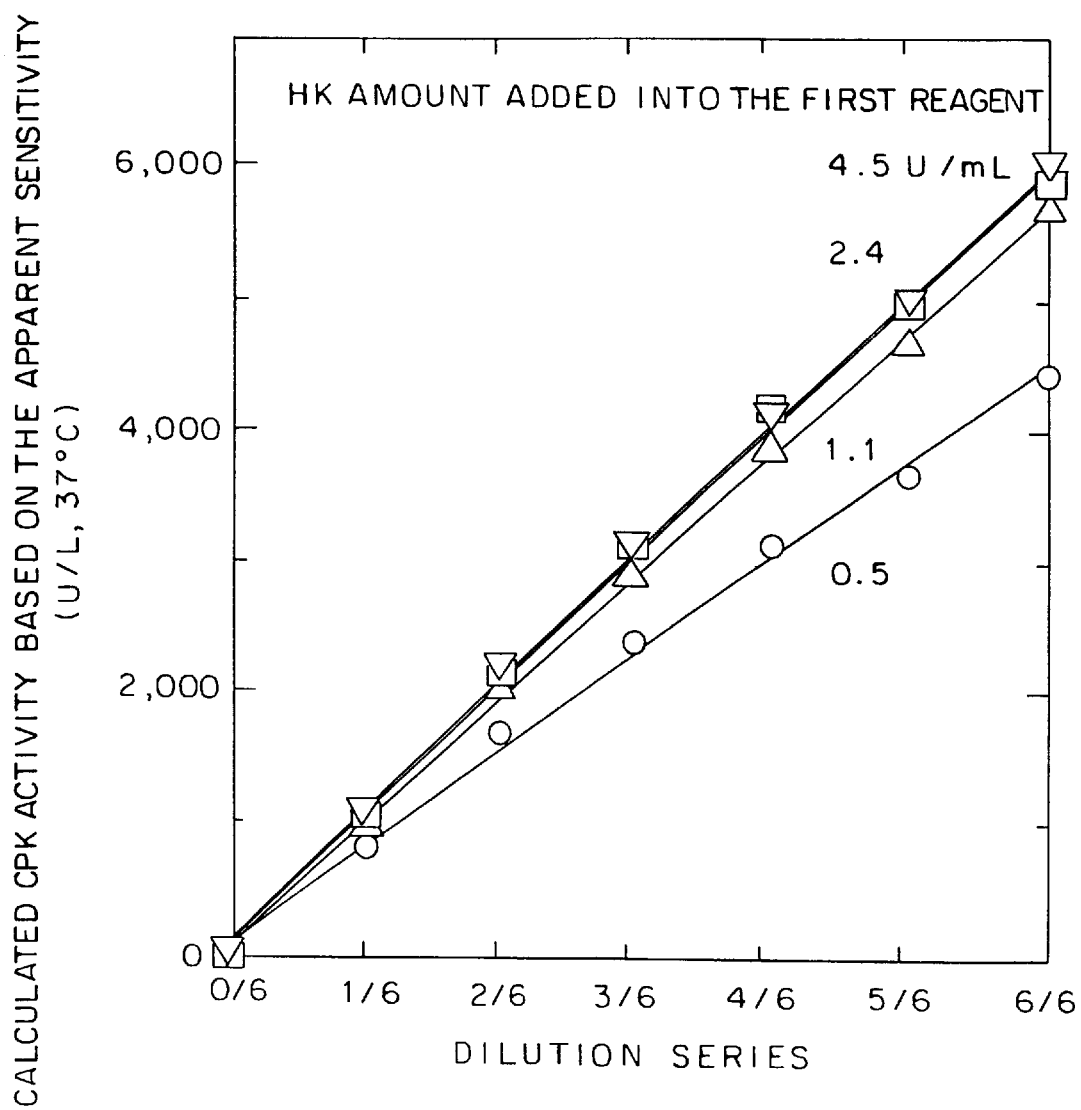
FIG. 5 shows relationship between dilution linearity of the sample and enzymatic amounts of the HK in determination of creatine kinase (CPK) activity.

In order to investigate the range which is linearly measurable in determination of creatine kinase activity, the relationship between the dilution linearity of the sample in determination of creatine kinase and the HK amount added into the First reagent was determined under the conditions given below, and the results are shown in FIG. 5.

Conditions:

(1) Sample

Creatine kinase derived from the skeletal muscle of rabbit was dissolved in an amount of 3,000 U per liter of the 50 mM Tris-HCl buffer under-mentioned and used (3,000 U/l in determination at 25° C.). Further, 6-step-dilutions of the obtained creatine kinase solution were also prepared and used.

(2) Creatine kinase dilution solution

Creatine kinase was diluted with 50 mM Tris-HCl buffer (pH 8.5) containing 1% BSA, 10 mM NAC, and 0.05% NaN$_3$ (in each example, the recommended method described in the transactions by Japanese Society of Clinical Chemistry was applied to the buffer for the storage tests and the varieties of the determination reagents used for investigation of the properties of the hexokinase).

EFFECT OF THE INVENTION

A novel hexokinase according to the present invention has high stability in solution, consequently it exerts a remarkable effect that the activity does not fall even in solution at high temperatures.

Therefore, the present enzyme can be stored for a long term even in a buffer and is quite advantageous to preparing a determination reagent and a kit for it, and furthermore, it can give an accurate measurement and extends shelf life of the merchandise to highly exert an economical effect.

We claim:

1. A purified hexokinase isolated from the thermophilic yeast *Kluyveromyces fragilis* IFO 1777, wherein said hexokinase retains at least 80% of its initial enzymatic activity in a buffered solution at 37° C. for 7 days, and said hexokinase has a greater substrate specificity for glucose and fructose compared to mannose, galactose, xylose, sorbitol and mannitol.

2. The hexokinase of claim 1, wherein said hexokinase has a molecular weight of about 60 kilodaltons based on gel filtration.

3. The hexokinase of claim 1, wherein said hexokinase has an isoelectric point at a pH value of 4.70.

4. A method for preparing the hexokinase of claim 1, comprising the steps of:

culturing the thermophilic yeast *Kluyveromyces fragilis* IFO 1777 to produce said hexokinase; and collecting said hexokinase from said culture.

5. A purified hexokinase having the following properties:

(1) retains at least 80% of its initial enzymatic activity in a buffered solution at 37° C. for 7 days;

(2) a greater substrate specificity for glucose and fructose as compared to mannose, galactose, xylose, sorbitol and mannitol;

(3) a molecular weight of about 60 kilodaltons based on gel filtration;

(4) an isoelectric point at pH 4.7D; and (5) is obtained from *Kluyveromyces fragilis* IFO 1777.

6. A method for preparing the hexokinase of claim 5, comprising the steps of:

culturing *Kluyveromyces fragilis* IFO 1777 capable of producing said hexokinase; and collecting said hexokinase produced by said culturing.

* * * * *